United States Patent [19]

Iwata et al.

[11] Patent Number: 4,621,090

[45] Date of Patent: Nov. 4, 1986

[54] ANTIFUNGAL COMPOSITIONS

[75] Inventors: Kazuo Iwata, Tokyo; Tetsuo Takematsu, Tochigi; Yuji Nonaka, Yamaguchi; Akira Nakanishi, Yamaguchi; Hideo Morinaka, Yamaguchi; Kenji Tsuzuki, Yamaguchi; Mitsuyuki Murakami, Yamaguchi; Takeshi Uotani, Yamaguchi, all of Japan

[73] Assignee: Toyo Soda Manufacturing Co., Ltd., Shinnanyo, Japan

[21] Appl. No.: 650,053

[22] Filed: Sep. 13, 1984

Related U.S. Application Data

[63] Continuation-in-part of Ser. No. 648,126, Sep. 7, 1984, abandoned.

[30] Foreign Application Priority Data

Sep. 13, 1983 [JP] Japan ............................ 58-167415

[51] Int. Cl.⁴ ............................................. A61K 31/44
[52] U.S. Cl. ................................... 514/332; 514/346
[58] Field of Search ................................ 514/346, 332

[56] References Cited
PUBLICATIONS
Chem. Abst., 15583g (1981).

Primary Examiner—Stanley J. Friedman
Attorney, Agent, or Firm—Oblon, Fisher, Spivak, McClelland & Maier

[57] ABSTRACT

An antifungal composition comprising an effective amount of carbamate derivative having the formula (I):

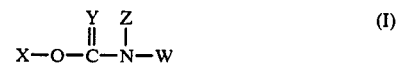

where
X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or a phenyl group having one or two of the same or different substituents selected from the group of halogen atom, lower alkyl, lower alkenyl, lower alkoxy, lower alkenyloxy, halogenated lower alkyl, lower alkylthio, lower alkylsulfonyl, lower alkylamino, nitro, and methylenedioxy;
Y is an oxygen atom or a sulfur atom;
Z is lower alkyl group;
W is pyridyl group having one or two of the same substituents selected from the group of lower alkyl, lower alkoxy, lower alkenyloxy, and lower alkylamino.

11 Claims, No Drawings

ANTIFUNGAL COMPOSITIONS

This application is a continuation-in-part of application Ser. No. 648,126 filed Sept. 7, 1984, now abandoned.

BACKGROUND OF THE INVENTION

1. Field of the Invention

The present invention relates to antifungal compositions containing new carbamate derivatives as the active ingredients.

2. Description of the Prior Art

Various carbamate derivatives are known to exhibit antifungal activity. Among them, especially known in the medical treatment against cutaneous fungal infections are, O-2-naphthyl N-methyl-N-3-methylphenylthiocarbamate (tolnaftate) and O-1,4-methano-1,2,3,4-tetrahydro-6-naphthyl N-methyl-N-3-methylphenylthiocarbamate (tolciclate).

The present inventors tested the novel N-pyridylcarbamate derivatives for their antimycotic activity and found certain N-pyridylcarbamate derivatives to exhibit a strong antifungal activity, which lead to the completion of the present invention.

SUMMARY OF THE INVENTION

The present invention thus provides antifungal compositions containing certain novel carbamate derivatives expressed by the following formula (I):

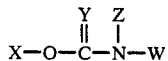

where
- X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or a phenyl group having one or two of the same or different substituents selected from the group of halogen atom, lower alkyl, lower alkenyl, lower alkoxy, lower alkenyloxy, halogenated lower alkyl, lower alkylthio, lower alkylsulfonyl, lower alkylamino, nitro, and methylenedioxy;
- Y is an oxygen atom or a sulfur atom;
- Z is a lower alkyl group;
- W is pyridyl group having one or two of the same substituents selected from the group of lower alkyl, lower alkoxy, lower alkenyloxy, and lower alkylamino.

In the lower alkyl, lower alkenyl, lower alkoxy, lower alkenyloxy, halogenated lower alkyl, lower alkylthio, lower alkylsulfonyl and lower alkylamino substituents listed above the term "lower" means 1 to 8 carbon atoms, preferably 1 to 5 carbon atoms, and more preferably 1 to 4 carbon atoms.

DETAILED DESCRIPTION OF THE INVENTION

The novel carbamate derivatives expressed by the formula (I) as an active ingredient of the antifungal composition of this invention can be produced in a process according to the following reaction schemes (1) and (2):

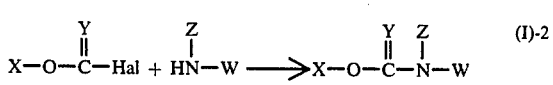

where
- X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or a phenyl group having one or two of the same or different substituents selected from the group of halogen atom, lower alkyl, lower alkenyl, lower alkoxy, lower alkenyloxy, halogenated lower alkyl, lower alkylthio, lower alkylsulfonyl, lower alkylamino, nitro, and methylenedioxy;
- Y is an oxygen atom or a sulfur atom;
- Z is a lower alkyl group;
- W is pyridyl group having one or two of the same substituents selected from the group of lower alkyl, lower alkoxy, lower alkenyloxy, and lower alkylamino;
- Hal is a halogen atom.

In the lower alkyl, lower alkenyl, lower alkoxy, lower alkenyloxy, halogenated lower alkyl, lower alkylthio, lower alkylsulfonyl and lower alkylamino substituents listed above the term "lower" means 1 to 8 carbon atoms, preferably 1 to 5 carbon atoms, and more preferably 1 to 4 carbon atoms.

The above reactions proceed in the presence of dehydrohalogenation agents, and further in the presence or absence of a reaction solvent, usually at a reaction temperature of 0° to 150° C. during the reaction time from about several minutes to 48 hours.

The dehydrohalogenation agents include alkali hydroxides such as sodium hydroxide, potassium hydroxide, and the like, alkaline earth hydroxide such as calcium hydroxide, and the like, alkali carbonates such as sodium carbonate, potassium carbonate, sodium hydrogen carbonate, potassium hydrogen carbonate, and the like, metal hydrides such as sodium hydride, and the like, tertiary amines such as triethylamine, dimethylaniline, pyridine, and the like. In the reaction scheme (2), the starting aminopyridine derivative may be used as a dehydrohalogenation agent.

Reaction solvents to be used in the reaction represented by schemes (1) and (2) include alcohols such as methanol, ethanol, isopropanol, and the like, ketones such as acetone, methylethylketone, and the like, aromatic hydrocarbons such as benzene, toluene, xylene, and the like, ethers such as ethyl ether, tetrahydrofuran, dioxane, and the like, halogenated hydrocarbons such as chlorobenzene, chloroform, carbon tetrachloride, dichloroethane, and the like, polar solvents such as dimethylformamide, dimethylsulfoxide, and the like.

The process for producing the carbamate derivatives by using formula (I) as an active ingredient of the antifungal composition of this invention will be explained in detail with reference to particular examples.

DESCRIPTION OF THE PREFERRED EMBODIMENTS

Example of synthesis 1

2-Naphthyl N-methyl-N-(4-methyl-2-pyridyl)carbamate (Compound No. 1)

A mixture of 1.85 g of N-methyl-N-(4-methyl-2-pyridyl)carbamoyl chloride, 1.44 g of 2-naphthol and 1.38 g of anhydrous potassium carbonate in methylethylketone was refluxed under heating for 48 hours. After the reaction mixture was cooled to room temperature, inorganic salts were removed by filtration and then methylethylketone was removed by distillation under a reduced pressure. The residue was purified by the column chromatography (silica gel, developed with ethyl acetate/benzene=1/9 (V/V) ), to obtain 2.37 g of oily 2-naphthyl N-methyl-N-(4-methyl-2-pyridyl)carbamate (yield 81%, refraction index $n_D^{25}$ 1.6191). The elementary analysis of this material was as follows:

| Elemental analysis: | | | |
|---|---|---|---|
| Found (%) | C: 74.09 | H: 5.60 | N: 9.32 |
| Calcd. (%) | C: 73.95 | H: 5.51 | N: 9.58 |

Example of synthesis 2

O-2-Naphthyl N-methyl-N-(6-methyl-2-pyridyl)thiocarbamate (Compound No. 2)

To a mixture of 1.22 g of 6-methyl-2-methylaminopyridine and 1.38 g of anhydrous potassium carbonate in 20 ml of acetone was added dropwise 2.23 g of 2-naphthylchlorothioformate in 20 ml of acetone under agitation at room temperature. The reaction mixture was stirred overnight at room temperature and inorganic salts were removed by filtration. After acetone was removed by distillation under a reduced pressure, the residue was purified by the column chromatography (silica gel, developed with ethyl acetate/benzene=1/9 (V/V), to obtain 2.62 g of O-2-naphthyl N-methyl-N-(6-methyl-2-pyridyl)thiocarbamate as a solid in a yield of 85%. A portion of the product was recrystallized from ethanol to give colorless crystals having a melting point of 149.5° C.–150.5° C. Elemental analysis of the crystals is given below.

| Elemental analysis: | | | |
|---|---|---|---|
| Found (%) | C: 69.89 | H: 5.19 | N: 8.89% |
| Calcd. (%) | C: 70.10 | H: 5.22 | N: 9.08% |

In a similar manner as that used in Examples of syntheses 1 and 2, novel carbamate derivatives expressed by the formula (I) as an active ingredient of the antifungal composition of this invention were synthesized. Typical examples of these carbamates, together with their physical properties are shown below, but the active ingredient of the antifungal composition of the present invention is not at all limited to these listed compounds.

These compounds will be referred to by their compound number in the descriptions.

| Compound No. | Compounds | Physical Property |
|---|---|---|
| (3) | O—2-Naphthyl N—methyl-N—(5-methyl-2-pyridyl)thiocarbamate | m.p. 122.5–124.5° C. |
| (4) | O—2-Naphthyl N—methyl-N—(4-methyl-2-pyridyl)thiocarbamate | m.p. 107–108.5° C. |
| (5) | O—2-Naphthyl N—methyl-N—(3-methyl-2-pyridyl)thiocarbamate | m.p. 127–129° C. |
| (6) | 2-Naphthyl N—methyl-N—(6-methoxy-2-pyridyl)carbamate | m.p. 140.5–142° C. |
| (7) | O—2-Naphthyl N—methyl-N—(6-methoxy-2-pyridyl)thiocarbamate | m.p. 95.5–97° C. |
| (8) | O—5,6,7,8-Tetrahydro-2-naphthyl N—methyl-N—(6-methyl-2-pyridyl)thiocarbamate | m.p. 137.5–139° C. |
| (9) | O—5-Indanyl N—methyl-N—(4-methyl-2-pyridyl)thiocarbamate N—methylthiocarbamate | m.p. 93.5–95° C. 96° C. |
| (11) | O—5,6,7,8-Tetrahydro-2-naphthyl N—(6-methoxy-2-pyridyl)-N—methylthiocarbamate | m.p. 98.5–99.5° C. |
| (12) | O—1,4-Methano-1,2,3,4-tetrahydro-6-naphthyl N—(6-methoxy-2-pyridyl)-N—methylthiocarbamate | m.p. 91–93° C. |
| (13) | 1,4-Methano-1,2,3,4-tetrahydro-6-naphthyl N—(6-methoxy-2-pyridyl)-N—methylcarbamate | m.p. 60.5–62° C. |
| (14) | O—2-Naphthyl N—methyl-N—(4,6,-dimethyl-2-pyridyl)thiocarbamate | m.p. 117–119° C. |
| (15) | O—5-Indanyl N—methyl-N—(4,6-dimethyl-2-pyridyl)thiocarbamate | m.p. 128–129° C. |
| (16) | O—4-t-Butylphenyl N—(6-methoxy-2-pyridyl)-N—methylthiocarbamate | m.p. 87–88° C. |
| (17) | O—2-Naphthyl N—(6-ethoxy-2-pyridyl)-N—methylthiocarbamate | m.p. 90.5–91° C. |
| (18) | O—4-t-Butylphenyl N—methyl-N—(6-methyl-2-pyridyl)thiocarbamate | m.p. 127–128.5° C. |
| (19) | O—4-t-Pentylphenyl N—(6-methoxy-2-pyridyl)-N—methylthiocarbamate | m.p. 113–114.5° C. |
| (20) | O—5,6,7,8-Tetrahydro-2-naphthyl N—(6-allyloxy-2-pyridyl)-N—methylthiocarbamate | m.p. 88–89° C. |
| (21) | O—1,4-Ethano-1,2,3,4-tetrahydro-6-naphthyl N—(6-methoxy-2-pyridyl)-N—methylthiocarbamate | m.p. 125–126.5° C. |
| (22) | O—3,4-Dimethylphenyl N—(6-methoxy-2-pyridyl)-N—methylthiocarbamate | m.p. 111–112° C. |
| (23) | O—2-Naphthyl N—(4-ethyl-2-pyridyl)-N—methylthiocarbamate | m.p. 99.5–101° C. |
| (24) | O—2-Naphthyl N—(6-ethyl-2-pyridyl)-N—methylthiocarbamate | m.p. 107–108° C. |
| (25) | O—2-Naphthyl N—methyl-N—(5,6-dimethyl-2-pyridyl)thiocarbamate | m.p. 108–109° C. |
| (26) | O—5-Indanyl N—methyl-N—(5,6-dimethyl-2-pyridyl)thiocarbamate | m.p. 102.5–104° C. |
| (27) | O—5,6,7,8-Tetrahydro-2-naphthyl N—methyl-N—(5,6-dimethyl-2-pyridyl)thiocarbamate | m.p. 98–99.5° C. |
| (28) | O—3-t-Butylphenyl N—(6-methoxy-2-pyridyl)-N—methylthiocarbamate | m.p. 85.5–86.5° C. |
| (29) | O—4-s-Butylphenyl N—(6-methoxy-2-pyridyl)-N—methylthiocarbamate | m.p. 52–53° C. |
| (30) | O—4-Isopropylphenyl N—(6-methoxy-2-pyridyl)-N—methylthiocarbamate | m.p. 55–56° C. |
| (31) | O—3-Methylphenyl N—(6-methoxy-2-pyridyl)-N—methylthiocarbamate | $n_D^{25}$ 1.6070 |
| (32) | O—3-Ethylphenyl N—(6-methoxy-2-pyridyl)-N—methylthiocarbamate | $n_D^{25}$ 1.6019 |
| (33) | O—4-Ethylphenyl N—(6-methoxy-2-pyridyl)-N—methylthiocarbamate | m.p. 69.5–70.5° C. |
| (34) | O—4-Bromophenyl N—(6-methoxy-2-pyridyl)-N—methylthiocarbamate | m.p. 87–88° C. |
| (35) | O—2-Naphthyl N—methyl-N—(6-dimethylamino-2-pyridyl)-thiocarbamate | m.p. 135–136° C. |
| (36) | O—4-t-Butylphenyl N—methyl-N—(6-dimethylamino-2-pyridyl)-thiocarbamate | m.p. 89.5–90.5° C. |
| (37) | O—3-t-Butylphenyl N—methyl-N—(6-methyl-2-pyridyl)thiocarbamate | m.p. 116–117.5° C. |
| (38) | O—4-Chloro-3-methylphenyl N—(6- | m.p. 93– |

-continued

| Compound No. | Compounds | Physical Property |
|---|---|---|
| | methoxy-2-pyridyl)-N—methylthiocarbamate | 94° C. |
| (39) | O—4-Ethyl-3-methylphenyl N—(6-methoxy-2-pyridyl)-N—methylthiocarbamate | m.p. 83–85° C. |
| (40) | O—5-Isopropyl-2-methylphenyl N—(6-methoxy-2-pyridyl)-N—methylthiocarbamate | $n_D^{25}$ 1.5814 |
| (41) | O—4-Isopropyl-3-methylphenyl N—(6-methoxy-2-pyridyl)-N—methylthiocarbamate | m.p. 67–68° C. |
| (41) | O—4-t-Butyl-3-methylphenyl N—(6-methoxy-2-pyridyl)-N—methylthiocarbamate | m.p. 97–98° C. |
| (43) | O—4-Trifluoromethylphenyl N—(6-methoxy-2-pyridyl)-N—methylthiocarbamate | m.p. 81– |
| (44) | O—4-Nitrophenyl N—(6-methoxy-2-pyridyl)-N—methylthiocarbamate | m.p. 91–92.5° C. |
| (45) | O—3-Chloro-4-methylphenyl N—(6-methoxy-2-pyridyl)-N—methylthiocarbamate | m.p. 103–105° C. |
| (46) | O—4-Bromo-3-methylphenyl N—(6-methoxy-2-pyridyl)-N—methylthiocarbamate | m.p. 105.5–107° C. |
| (47) | O—3-Trifluoromethylphenyl N—(6-methoxy-2-pyridyl)-N—methylthiocarbamate | m.p. 71–72° C. |
| (48) | O—3-Isopropylphenyl N—(6-methoxy-2-pyridyl)-N—methylthiocarbamate | m.p. 50–51° C. |
| (49) | O—3-Bromophenyl N—(6-methoxy-2-pyridyl)-N—methylthiocarbamate | m.p. 69–69.5° C. |
| (50) | O—3,4-Dichlorophenyl N—(6-methoxy-2-pyridyl)-N—methylthiocarbamate | m.p. 78–79° C. |
| (51) | O—4-Chloro-3-methylphenyl N—methyl-N—(6-methyl-2-pyridyl)thiocarbamate | m.p. 134–136° C. |
| (52) | O—3,4-Dimethylphenyl N—methyl-N—(4-methyl-2-pyridyl)thiocarbamate | m.p. 113–114° C. |
| (53) | O—4-Methylphenyl N—(6-methoxy-2-pyridyl)-N—methylthiocarbamate | m.p. 66.5–67.5° C. |
| (54) | O—4-Chloro-3-methoxyphenyl N—(6-methoxy-2-pyridyl)-N—methylthiocarbamate | m.p. 64.5–65.5° C. |
| (55) | O—4-Chloro-3-allyloxyphenyl N—(6-methoxy-2-pyridyl)-N—methylthiocarbamate | m.p. 116.5–117.5° C. |
| (56) | O—4-Isopropenylphenyl N—(6-methoxy-2-pyridyl)-N—methylthiocarbamate | m.p. 93–93.5° C. |
| (57) | O—3-t-Butylphenyl N—methyl-N—(6-dimethylamino-2-pyridyl)thiocarbamate | $n_D^{25}$ 1.6002 |
| (58) | O—4-t-Butylphenyl N—methyl-N—(6-methylamino-2-pyridyl)thiocarbamate | m.p. 113–114° C. |
| (59) | O—3-t-Butylphenyl N—methyl-N—(6-methylamino-2-pyridyl)thiocarbamate | m.p. 73–74° C. |
| (60) | O—4-Methoxyphenyl N—(6-methoxy-2-pyridyl)-N—methylthiocarbamate | m.p. 97.5–98.5° C. |
| (61) | O—4-Ethoxyphenyl N—(6-methoxy-2-pyridyl)-N—methylthiocarbamate | m.p. 96.5–97.5° C. |
| (62) | O—4-Methylthiophenyl N—(6-methoxy-2-pyridyl)-N—methylthiocarbamate | m.p. 106.5–108° C. |
| (63) | O—3,4-Methylenedioxyphenyl N-13 (6-methoxy-2-pyridyl)-N—methylthiocarbamate | m.p. 102.5–103.5° C. |
| (64) | O—5,6,7,8-Tetrahydro-2-naphthyl N—ethyl-N—(6-methoxy-2-pyridyl)thiocarbamate | $n_D^{25}$ 1.6030 |
| (65) | O—4-Propylphenyl N—(6-methoxy-2-pyridyl)-N—methylthiocarbamate | m.p. 40–42° C. |
| (66) | O—Methyl-4-nitrophenyl N—(6-methoxy-2-pyridyl)-N—methylthiocarbamate | m.p. 59–61° C. |
| (67) | O—3-Methyl-4-methylthiophenyl N—(6-methoxy-2-pyridyl)-N—methylthiocarbamate | m.p. 78–79° C. |
| (68) | O—4-Trifluoromethylphenyl N—(6-dimethylamino-2-pyridyl)-N—methylthiocarbamate | m.p. 74–76° C. |
| | dimethylamino-2-pyridyl)-N—methylthiocarbamate | 76° C. |
| (69) | O—3-Dimethylaminophenyl N—(6-methoxy-2-pyridyl)-N—methylthiocarbamate | m.p. 111–113° C. |
| (70) | O—4-Methylsulfonylphenyl N—(6-methoxy-2-pyridyl)-N—methylthiocarbamate | m.p. 121–122° C. |
| (71) | O—4-Chloro-3-ethylphenyl N—(6-methoxy-2-pyridyl)-N—methylthiocarbamate | m.p. 69.5–70.5° C. |
| (72) | O—4-Bromo-3-isopropylphenyl N—(6-methoxy-2-pyridyl)-N—methylthiocarbamate | n.p. 82– |
| (73) | O—4-Bromo-3-t-butylphenyl N—(6-methoxy-2-pyridyl)-N—methylthiocarbamate | m.p. 117–119° C. |
| (74) | O—2-Quinolyl N—(6-methoxy-2-pyridyl-N—methylthiocarbamate | m.p. 106–108° C. |
| (75) | O—4-Bromo-3-ethylphenyl N—(6-methoxy-2-pyridyl)-N—methylthiocarbamate | m.p. 84–85° C. |

The antifungal composition of the present invention can exhibit antibacterial and antiprotozoa activity as well as the antifungal activity.

The fungi referred to here include, for example, Trichophyton asteroides, Trichophyton cerebriformis, Trichophyton coccineum, Trichophyton crateriforme, Trichophyton ferrugineum, Trichophyton glabrum, Trichophyton interdigitale, Trichophyton mentagraphytes, Trichophyton pedis, Trichophyton quinckeanum, Trichophyton rosaceum, Trichophyton rubrum, Trichophyton schoenleini, Trichophyton violaceum, Microsporum audouinii, Microsporum canis, Microsporum gypseum, Microsporum sapporoensis, Epidermophyton floccosum, Sporothrix schenkii, Fonsecaea pedrosoi, Fonsecaea compactum, Phialophora verrucosa, Phialophora dermatitidis, Histoplasma capsulatum, Histoplasma duboisii, Blastmyces dermatitidis, Paracoccidioides brasiliensis, Aspergillus fumigatus, Aspergillus niger, Candida albicans, Candida tropicalis, Candida pseudotropicalis, Candida krusei, Candida parapsilosis, Candida guilliermondii, Cryptococcus neoformans, Mucor mucedo, Penicillium notatum, Rhizopus nigricans, Rhodotorula glutinis, Fusarium pedrosoi, Piricularia oryzae, and the like.

The bacteria include, for example, Actinomyces bovis, Actinomyces israelii, Actinomyces naeslumdii, Actinomyces odontolyticus, Actinomyces viscosus, Nocardia asteroides, Nocardia brasiliensis, Malassezia furfur, Corynebacterium minutissimum, Staphylococcus aureus, Staphylococcus epidermidis, Staphylococcus saprophyticus, and the like.

The protozoa include, for example, Trichomonas vaginalis and Trichomonas foetus, and the like.

The antifungal agents of this invention exhibit activity against various pathogens of cited fungi, bacteria, and protozoa which infect human beings, animals and plants. The microorganisms mentioned above are a part of those which are sensitive to the antifungal compositions of this invention.

The antifungal compositions of this invention can exhibit a wide spectrum of antifungal activity as mentioned above, particularly toward skin fungi such as Trichophyton species, Microsporum species and Epidermophyton species, and show a strong supression toward Aspergillus and Fusarium species.

When the antifungal compositions of this invention are medically applied toward skin fungi, the carbamate derivatives represented by formula (I) as the active ingredient are either dissolved in an appropriate inert carrier (for example, solvent, diluent or filler) or dispersed or adsorbed, and then, if necessary, they are mixed with an emulsifier, dispenser, suspender, developer, penetrant, wetting agent, viscosity liquifier, and stabilizer. They may be used in the form of a liquid, granule, emulsoid, suspensoid, ointment, powder, spray, and cataplasm, and may be administered orally, non-orally or topically.

As an inert carrier, water, alcohols, such as methanol, ethanol, glycol, glycerin, and the like, glycol ethers such as ethyleneglycol monomethyl ether, ethyleneglycol monoethyl ether, diethyleneglycol monomethyl ether, and the like, polar aprotic solvents such as DMF, DMSO, and the like, ointment bases such as yellow vaseline, white vaseline, and the like, waxes such as polyethyleneglycol 4000, whale wax, wood wax, and the like can be used.

The antifungal compositions of this invention are not restricted with respect to the content of effective components, but the content may be 0.01 to 70% by weight, preferably 0.1 to 5% by weight, to the total weight of preparation. Further, the antifungal compositions of this invention may contain keratolytic agents, additional antifungal agents, and antibacterial agents such as undecylenic acid, gliseofulvin, fezatione, clotrimazole, siccanin, ciclopirox olamine, tolciclate, pyrrolnitrin, flucytosine, phenyl iodoundecynoate, lisium, hexachlorophene, tolnaftate, salicyclic acid, methyl salicylate, penicillins, cephalosporins, thienamycins, streptomycin, fradiomycin, and tetracyclins.

The following examples will demonstrate that the carbamate derivatives by the formula (I) as the active ingredient of the antifungal compositions of this invention exhibit a high activity toward fungi, and the antifungal compositions of this invention are useful for the medical treatment of animals who have been infected by fungi while also being harmless to the animals.

EXAMPLE 1

Anti-*Trichophyton mentagraphytes* activity test

The activity was tested by the 10 time-step dilution test, using the Sabouraud's dextrose agar culture medium (2% dextrose, 1% pepton and 1.5% agar; pH 6.5±). A platinum loopful (about 10 μl) spore suspension (prepared from a reserved strain of *Trichlophyton mentagraphytes* and containing $1 \times 10^6$ cells/ml) was applied in the form of drawn lines on a plate of a culture medium containing the active ingredients. The culture medium plate was kept at 27° C. for a week and then visually observed to see if any colonies had formed. The minimum inhibitory concentration was defined as the minimum concentration with which formation of distinct colonies on the culture medium plate was not observed.

The results are shown in Table 1.

EXAMPLE 2

Growth inhibition test against various fungi other than *Trichophyton mentagraphytes* and against *Cryptococcus neoformans*

The fungi species used in this test were *Trichophyton violaceum*, *Microsporum canis*, *Microsporum gypseum*, *Epidermophyton floccosum*, *Aspergillus fumigatus*, *Fusarium pedrosoi*, and so on. According to the process in Example 1, minimum inhibitory concentrations were recorded after two days, a week and two weeks cultivation. The results are shown in Table 2.

TABLE 1

Results of the growth inhibition test against *Trichophyton mentagraphytes*

| Compound No. | Minimum inhibitory concentration (μg/ml) Tested strain | | Compound No. | Minimum inhibitory concentration (μg/ml) Tested strain | |
|---|---|---|---|---|---|
| | MTU-19024 | MTU-19031 | | MTU-19024 | MTU-19031 |
| 2 | 0.5 | 0.5 | 34 | 0.5 | 0.05 |
| 7 | 0.05 | 0.05 | 35 | 0.5 | 0.5 |
| 8 | 0.5 | 0.5 | 36 | 0.5 | 0.5 |
| 10 | 0.5 | 0.05 | 38 | 0.5 | 0.05 |
| 11 | 0.05 | 0.05 | 39 | 0.5 | 0.5 |
| 12 | 0.5 | 0.5 | 41 | 0.5 | 0.5 |
| 13 | 0.5 | 0.5 | 43 | 0.5 | 0.05 |
| 14 | 0.5 | 0.5 | 46 | 0.5 | 0.5 |
| 15 | 0.5 | 0.5 | 48 | 0.5 | 0.5 |
| 16 | 0.5 | 0.5 | 50 | 0.5 | 0.5 |
| 19 | 0.5 | 0.5 | 53 | 0.5 | 0.5 |
| 21 | 0.5 | 0.5 | 56 | 0.5 | 0.5 |
| 22 | 0.5 | 0.5 | 58 | 0.5 | 0.5 |
| 25 | 0.5 | 0.5 | 62 | 0.5 | 0.05 |
| 26 | 0.5 | 0.5 | 65 | 0.5 | 0.5 |
| 27 | 0.5 | 0.5 | 66 | 0.5 | 0.5 |
| 28 | 0.5 | 0.5 | 67 | 0.5 | 0.5 |
| 30 | 0.5 | 0.5 | 68 | 0.5 | 0.5 |
| 33 | 0.5 | 0.05 | | | |

TABLE 2

Results of the growth inhibition test against various fungi other than *Trichophyton mentagraphytes* and against *Cryptococcus neoformans*
Minimum inhibitory concentration (μg/ml)

| Strain tested | Compound No. | | | | | | | |
|---|---|---|---|---|---|---|---|---|
| | 7 | | 11 | | 28 | | 48 | |
| *Trichophyton violaceum* MTU-19021 | 0.05** | 0.05*** | 0.05** | 0.05*** | 0.5** | 0.5*** | 0.5** | 0.5*** |
| *Microsporum canis* MTU-20010 | 0.05** | 0.05*** | 0.05** | 0.05*** | 0.5** | 0.5*** | 0.5** | 0.5*** |
| *Microsporum gypseum* MTU-20005 | 0.05** | 0.05*** | 0.5** | 0.05*** | 0.5** | 0.5*** | 0.5** | 0.5*** |
| *Epidermophyton floccosum* MTU-21007 | | 0.05*** | | 0.05*** | | 0.5*** | | 0.5*** |
| *Fonsecaea compactum* MTU-22023 | 0.5** | 0.5*** | 0.5** | 0.5*** | — | | — | |
| *Phialophora verrucosa* MTU-23001 | 0.5** | 0.5*** | 0.5** | 0.5*** | — | | — | |
| *Histoplasma capsulatum* MTU-16001 | | 0.5*** | | 0.5*** | — | | — | |
| *Blastomyces dermatitidis* | | 0.5*** | | 0.5*** | — | | — | |

TABLE 2-continued

Results of the growth inhibition test against various fungi other than
Trichophyton mentagraphytes and against Cryptococcus neoformans
Minimum inhibitory concentration (μg/ml)

| Strain tested | Compound No. | | | |
|---|---|---|---|---|
| | 7 | 11 | 28 | 48 |
| MTU-17009 | | | | |
| *Aspergillus fumigatus* MTU-06002 | 0.5** | 0.5** | — | — |
| *Aspergillus niger* MTU-06051 | 0.05** | 0.05*** | 0.05** | 0.05*** | — | — |
| *Fusarium pedrosoi* MTU-22009 | 0.5** | — | — | — |
| *Cryptococcus neoformans* MTU-13002 | 0.05* | 0.5* | — | — |

*After 2 days cultivation at 27° C. minimum inhibitory concentration was recorded.
**After 7 days cultivation at 27° C. minimum inhibitory concentration was recorded.
***After 14 days cultivation at 27° C. minimum inhibitory concentration was recorded.

EXAMPLE 3

Medical treatment test of the antifungal composition of this invention against experimental *Trichophyton mentagrophytes* infection on guinea pigs Skin hairs on the back of white guinea pigs of a 400–500 g body weight were cut by a hair clipper and 0.1 ml of a spore suspension (containing $1 \times 10^7$ cell/ml) of *Trichophyton mentagraphytes* was inoculated. A polythyleneglycol emulsion containing 1% of an active ingredient was applied once a day, every day, after the inoculation. The result was judged by the appearance of symptoms of the infected site and the reversed cultivation. Table 3 shows the results of the medical treatment as compared with those of control guinea pigs.

TABLE 3

Medical treatment of a guinea pig experimentally infected with *Trichophyton mentagraphytes*

| Compound No. | Scope of symptoms (0–4) Days after the infection | | | | | Reversed cultivation |
|---|---|---|---|---|---|---|
| | 5 | 9 | 13 | 17 | 21 | |
| Not administered | 0.16 | 1.5 | 2.5 | 1.5 | 0.83 | 29/60 |
| 7 | 0 | 1.33 | 1.66 | 0.66 | 0.33 | 1/60 |
| 11 | 0.66 | 2.0 | 2.0 | 0 | 0 | 1/60 |

Each of the groups consisting of 6 guinea pigs were used in the test. Symptoms were expressed according to Weinsteins' expression (Antimicrobial Agents Chemotheraphy, 1964, 595 (1965) ); a score of 0 was given when no symptoms were observed, and scores +1 to +4 for increasing strengths of symptoms. The results were expressed by the mean values. As a reversed cultivation, skin of the innoculated site was taken and then cut into 10 pieces which were then cultivated on Sabouraud's dextrose agar plates for 14 days at a temperature of 27° C.

EXAMPLE 4

Acute toxicity test and skin irritation test

The acute toxicity was tested by applying active ingredients of the antifungal compositions of this invention as shown in Table 4 to ICR mice (male, age-5 weeks, 25 g ±weight, 5 mice in each group). The results obtained are shown in Table 4. Observation continued for 3 more weeks starting from the last administration. As seen in the Table, acute toxicity and irritation of the skin were not observed.

TABLE 4

The results of acute toxicity test and skin irritation test using ICR mice

| Administration | Dose and period | Observation | Compound | |
|---|---|---|---|---|
| | | | 7 | 11 |
| Oral* | 500 mg/kg** once a day administered for 6 consecutive days | Number of deaths | 0 | 0 |
| | | | 0 | 0 |
| | | symptomatic weight decrease | 0 | 0 |
| Intraperitoneal | 500 mg/kg** once | Number of deaths | 0 | 0 |
| | | | 0 | 0 |
| | | symptomatic weight decrease | 0 | 0 |
| | 100 mg/kg** once a day administered for 6 consecutive days | Number of deaths | 0 | 0 |
| | | | 0 | 0 |
| | | symptomatic weight decrease | 0 | • |
| Cutaneous | 1%*** Direct application once a day for 14 consecutive days | Number of skin irritation symptoms | 0 | 0 |

*A stomach tube was used.
**In a 0.3% emulsion in CMC (carboxymethyl cellulose).
***In a suspension in polyethyleneglycol.

What is claimed is:

1. A method for controlling fungus, comprising administering an effective amount of a compound of formula (I)

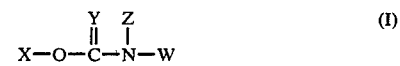

wherein
X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or a phenyl group having one or two of the same or different substituent selected from the group consisting of halogen atoms, lower alkyls, lower alkenyls, lower alkoxys, lower alkenyloxys, halogenated lower alkyls, lower alkylthios, lower alkylsulfonyls, lower alkylaminos, nitro and methylenedioxys;
Y is an oxygen atom or a sulfur atom;
Z is a lower alkyl group; and
W is a pyridyl group having one or two of the same substituents selected from the group consisting of lower alkyls, lower alkoxys, lower alkenyloxys and lower alkylaminos.

2. The method of claim 1, wherein said fungus comprises *Trichophyton mentagrophytes, Trichophyton violaceum, Microsporum canis, Microsporum gypseum, Epidermophyton floccosum, Fonsecaea compactum, Phialophora verrucosa, Histoplasma capsulatum, Blastomyces dermatitidis, Aspergillus fumigatus, Aspergillus niger, Fusarium pedrosoi* or *Cryptococcus neoformans*.

3. The method of one of claims 1, comprising administering O-2-naphthyl N-methyl-N-(6-methoxy-2-pyridyl)thiocarbamate.

4. The method of one of claims 1, comprising administering O-5-indanyl N-(6-methoxy-2-pyridyl)-N-methyl-thiocarbamate.

5. The method of one of claims 1, comprising administering O-5,6,7,8-tetrahydro-2-naphthyl (N-(6-methoxy-2-pyridyl)-N-methylthiocarbamate.

6. The method of one of claims 1, comprising administering O-4-ethylphenyl N-(6-methoxy-2-pyridyl)-N-methylthiocarbamate.

7. The method of one of claims 1, comprising administering O-4-bromophenyl N-(6-methoxyl-2-pyridyl)-N-methylthiocarbamate.

8. The method of one of claims 1, comprising administering O-4-chloro-3-methylphenyl N-(6-methoxyl-2-pyridyl)-N-methylthiocarbamate.

9. The method of one of claims 1, comprising administering O-4-trifluoromethyl N-(6-methoxy-2-pyridyl)-N-methylthiocarbamate.

10. The method of one of claims 1, comprising administering O-4-methylthiophenyl N-(6-methoxy-2-pyridyl)-N-methylthiocarbamate.

11. A composition comprising:
(i) an antifungal effective amount of a compound of formula (I)

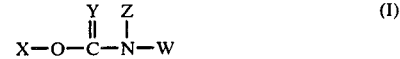

wherein
X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or a phenyl group having one or two of the same or different substituents selected from the group consisting of halogen atoms, lower alkyls, lower alkenyls, lower alkoxys, lower alkenyloxys, halogenated lower alkyls, lower alkylthios, lower alkylsulfonyls, lower alkylaminos, nitro and methylenedioxys;
Y is an oxygen atom or a sulfur atom;
Z is a lower alkyl group; and
W is a pyridyl group having one or two of the same substituents selected from the group consisting of lower alkyls, lower alkoxys, lower alkenyloxys and lower alkylaminos; and
(ii) an inert carrier suitable for antifungal applications.

* * * * *